United States Patent [19]
Haselton, III et al.

[11] Patent Number: 6,017,758
[45] Date of Patent: Jan. 25, 2000

[54] DMNPE CAGED NUCLEIC ACID AND VECTOR

[75] Inventors: Frederick R. Haselton, III, Nashville, Tenn.; J. Steven Alexander, Shreveport, La.

[73] Assignee: Vanderbilt University, Nashville, Tenn.

[21] Appl. No.: 09/026,794

[22] Filed: Feb. 20, 1998

Related U.S. Application Data

[60] Provisional application No. 60/038,676, Feb. 20, 1997.

[51] Int. Cl.[7] .............................. C12N 15/63; C12N 1/00; C12N 5/10; C12N 15/11
[52] U.S. Cl. ....................... 435/325; 435/320.1; 435/243; 435/410; 536/23.1
[58] Field of Search ........................ 536/23.1; 435/320.1, 435/325, 410, 243

[56] References Cited

U.S. PATENT DOCUMENTS

| | | | |
|---|---|---|---|
| 5,256,648 | 10/1993 | Gasparro et al. | 514/44 |
| 5,489,678 | 2/1996 | Fodor et al. | 536/22.1 |
| 5,635,608 | 6/1997 | Haugland et al. | 536/1.11 |
| 5,801,001 | 9/1998 | Sager et al. | 435/7.23 |

OTHER PUBLICATIONS

Ammala et al, Biochimica et Biophysica Acta, vol. 1092, pp. 347–349, 1991.
Ishihara, A., et al. "Photoactivation of caged compounds in single living cells: an application to the study of cell locomotion." *Biotechniques* 23:268–274, 1997.
McGall, G., et al. "Light–directed synthesis of high–density oligonucleotide arrays using semiconductor photoresistors." *Proc. Nat. Acad. Sci.* 93:13555–13560, 1996.
Molecular Probes Article (MP 2516). "1–(4, 5–Dimethoxy–2–Nitrophenyl) Diazoethane (DMPNPE) Generation Kit (D–2516)" pp. 1–2, Mar. 13, 1996.
Molecular Probes Article (MP 1037). "Photoactivatable ("Caged") Probes, Unique Tools for Cell Biology and Neurosciences" pp. 1–4, Jun. 18, 1996.
McCray, J.A., et.al. "Properties and Uses of Photoreactive Caged Compounds" *Annual Review of Biophysics & Biophysical Chemistry* 18:239–270, 1989.
Walker J.W., et al. "Photolabile 1–(2–Nitrophenyl)ethyl phosphate esters of adenine nucleotide analogues. Synthesis and mechanism of photolysis." *J. Am. Chem. Soc.* 110:7170–7177, 1988.
Wootton J.F., and Trentham D.R. "Caged compounds to probe the dynamics of cellular processes: Synthesis and properties of some novel photosensitive P–2–nitrobenzyl esters of nucleotides." *Photochemical Probes in Biochemistry*, PE Nielson (ed), Kluwer Acad. Pub., Norwell, MA, pp. 277–296, 1988.
Kaplan, J.H., et al. "Rapid photolytic release of ATP protected analogue: utilization by the Na:K pump of human red blood cell ghosts." *Biochemistry* 17:1929–1935, 1978.

*Primary Examiner*—Terry McKelvey
*Attorney, Agent, or Firm*—Needle & Rosenberg, P.C.

[57] ABSTRACT

The present invention provides an isolated nucleic acid covalently linked to a photolabile caging group which reversibly prevents expression of the nucleic acid. The present invention further provides a method of selectively expressing a nucleic acid in a cell, comprising: a) covalently linking the nucleic acid to a photolabile caging group which reversibly prevents expression of the nucleic acid; b) introducing the nucleic acid of step (a) into the cell; and c) exposing the cell of step (b) to light, whereby exposure to the light unlinks the nucleic acid and the caging group and the nucleic acid is selectively expressed in the cell. Additionally provided is a method of selectively regulating the expression of an endogenous nucleic acid comprising: a) covalently linking a nucleic acid encoding an antisense nucleic acid to a photolabile caging group which reversibly prevents expression of the nucleic acid; b) introducing the nucleic acid of step (a) into the cell; and c) exposing the cell of step (b) to light, whereby exposure to the light unlinks the nucleic acid and the caging group and the nucleic acid is selectively expressed in the cell as an antisense nucleic acid which can bind to and inactivate a complementary nucleic acid within the cell.

5 Claims, No Drawings

DMNPE CAGED NUCLEIC ACID AND VECTOR

This application claims priority to Provisional Application Ser. No. 60/038,676, which was filed on Feb. 20, 1997.

This invention was made in part with government support under NIH grant number AR419343 as a Pilot and Feasibility Project, awarded by the National Institutes of Health. The government has certain rights in the invention.

BACKGROUND OF THE INVENTION

1. Field of the Invention

The present invention relates to selective expression of genes useful in gene therapy protocols via photoactivation. In particular, the present invention provides a means of selectively expressing genes in specific cells, comprising delivering "caged" (inactivated) nucleic acid to cells and "uncaging" (activating) the nucleic acid by exposure of the targeted cells to light, thereby allowing temporally controlled expression of exogenous nucleic acid only in targeted cells or selectively regulating endogenous gene expression.

2. Background Art

The as yet unrealized goal of in vivo gene therapy is the expression of exogenous genetic material within only a target cell population. Successful in vivo gene therapy must overcome two challenges: 1) delivery of genes to the specific target cell population and 2) subsequent expression only within these cells. Viral and nonviral technologies for targeted delivery of genes have been evaluated. These include localized injection in skeletal muscle (Manthrope et al., 1993; reviewed in Brown et al., 1996), targeting of liposomes by incorporating antibodies to unique cell surface markers in the liposome outer surface (reviewed in Torchilin, 1996) and use of viruses with naturally selected sub-population targets, such as adenovirus for the bronchial epithelium (Rosenfeld et al., 1993). Although all of these strategies require that each target cell population be uniquely defined, the potential utility has kept interest high. Because of immune responses with adenovirus, safety issues with retroviruses and the poor targeting ability of liposomes, none of these strategies has proven suitable in its current form for targeted delivery and expression of genes.

In addition, targeted post-delivery expression strategies have been attempted (reviewed by Yarranton, 1992). These strategies involve delivery of nucleic acids comprising elements which can be broadly classified into 1) inducers triggered by changes in the cellular environment (cell milieu inducers) and 2) promoters which induce expression only within specific tissues. Cell milieu inducers can include promoters sensitive to metal concentration (Searle et al., 1985; Mayo et al., 1982), tetracycline (Furth et al., 1994; Gossen et al., 1995), hormones (Hynes et al., 1981; Andres et al., 1987) and the insect molting hormone ecdysone (No et al., 1996). However, the cell milieu inducers cannot be used to target sub-populations of cells, since all transfected cells respond to such changes in the cellular environment. Furthermore, unique tissue-specific promoters (reviewed by Hart, 1996; Stein et al., 1996) must be developed for each individual target cell population.

Photosensitive precursors or "caging" groups are molecules which bind an "effector" molecule through a covalent bond to the photosensitive precursor group, thereby reversibly rendering the effector molecule inert (McCray et al., 1989). The term "caged" is merely descriptive of the photo release property of these groups and does not refer to physical trapping of the inactivated substance within a crystal lattice. Caging groups have been used in a number of biological studies to study cell motility, muscle fibers, active transport proteins, biological membranes and other intracellular responses (e.g. Ishihara et al., 1997; Lee et al., 1997; Patton et al., 1991; see review by McCray et al., 1989). Caging groups have also been used in the caging of nucleotide analogues (Walker et al., 1988) and the synthesis of bio-chip arrays (McGall et al., 1996). Classically, caging groups have been used to study the time course of cellular responses induced by a step change in a local concentration of caged and subsequently, inactivated biochemical species, e.g. caged ATP. A rapid localized increase in concentration or activity of the caged substance is achieved by application of a directed pulse of light, which releases the bio-chemical inactivating group and returns the caged species to its biologically active state. In the case of caged ATP, this results in a localized high concentration of ATP. However, neither the caging of nucleic acids for selective regulation of gene expression nor the use of caged nucleic acids in therapeutic applications such as gene therapy have been described.

The present invention overcomes previous shortcomings in gene therapy technology by providing methods whereby caged genes or caged proteins can be delivered nonspecifically to cells and the genes or proteins in selected cells can be activated by exposure to light, thereby limiting the expression of genes or activity of exogenous proteins to selected cells. The methods of this invention can be employed to treat a variety of disease states and genetic disorders.

SUMMARY OF THE INVENTION

The present invention provides an isolated nucleic acid covalently linked to a photonlabile caging group which reversibly prevents expression of the nucleic acid.

The present invention further provides a method of selectively expressing a nucleic acid in a cell, comprising: a) covalently linking the nucleic acid to a photolabile caging group which reversibly prevents expression of the nucleic acid; b) introducing the nucleic acid of step (a) into the cell; and c) exposing the cell of step (b) to light, whereby exposure to the light unlinks the nucleic acid and the caging group and the nucleic acid is selectively expressed in the cell.

The present invention additionally provides a method of selectively regulating the expression of an endogenous nucleic acid comprising: a) covalently linking a nucleic acid encoding an antisense nucleic acid to a photolabile caging group which reversibly prevents expression of the nucleic acid; b) introducing the nucleic acid of step (a) into the cell; and c) exposing the cell of step (b))to light, whereby exposure to the light unlinks the nucleic acid and the caging group and the nucleic acid is selectively expressed in the cell as an antisense nucleic acid which can bind to and inactivate a complementary nucleic acid within the cell.

Various other objectives and advantages of the present invention will become apparent from the following detailed description.

DETAILED DESCRIPTION OF THE INVENTION

As used herein, "a" or "an" can mean multiples.

The present invention provides a novel strategy for localized targeting of gene expression based on delivering reversibly inactivated genes to cells which can be selectively expressed in targeted cells upon activation of the genes by exposure to light. Transcription of the genes in cells is blocked by biochemical modification of the plasmid nucleic acid with a "caging" group. Activation of transcription is achieved by "uncaging" the plasmid by exposure to light.

Thus, the present invention provides an isolated nucleic acid covalently linked to a photolabile caging group which reversibly prevents expression of the nucleic acid. As used herein, "nucleic acid" refers to single- or double-stranded molecules which may be DNA, comprising two or more nucleotides comprised of the nucleotide bases A, T, C and G, or RNA, comprised of the bases A, U (substitute for T), C and G. The nucleic acid may represent a coding strand or its complement. Nucleic acids may be identical in sequence to a sequence which is naturally occurring or may include alternative codons which encode the same amino acid as that which is found in a naturally occurring sequence (Lewin, 1994). Furthermore, nucleic acids may include codons which represent conservative substitutions of amino acids as are well known in the art. With regard to gene therapy applications, the nucleic acid can comprise a nucleotide sequence which encodes a gene product which is meant to function in the place of a defective gene product and restore normal function to a cell which functioned abnormally due to the defective gene product. Alternatively, the nucleic acid may encode a gene product which was not previously present in a cell or was not previously present in the cell at a therapeutic concentration, whereby the presence of the exogenous gene product or increased concentration of the exogenous gene product imparts a therapeutic benefit to the cell and/or to a subject. For example, the nucleic acid of this invention can include but is not limited to, a gene encoding a gene product that promotes cell killing, a gene encoding a gene product involved in inherited disorders, a gene encoding a gene product that promotes wound repair, a gene encoding a gene product which promotes cell-cell adhesion and a gene encoding a gene product which modulates cellular signals.

As used herein, the term "isolated" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by techniques such as cell lysis followed by phenol plus chloroform extraction, followed by ethanol precipitation of the nucleic acids (Michieli et al., 1996). The nucleic acids of this invention can be isolated from cells according to methods well known in the art. Alternatively, the nucleic acids of the present invention can be synthesized according to standard protocols well described in the literature.

Also as used herein, "expression of the nucleic acid" means transcription of DNA into RNA, translation of RNA into an amnino acid sequence with subsequent modifications to produce a functional polypeptide or both transcription and translation.

The nucleic acid of this invention can be part of a recombinant nucleic acid comprising any combination of restriction sites and/or functional elements as are well known in the art which facilitate molecular cloning, expression and other recombinant DNA manipulations. Thus, the present invention further provides a recombinant nucleic acid comprising the nucleic acid of the present invention. In particular, the nucleic acid can be present in a vector and the vector can be present in a cell, which can be a cell cultured in vitro or a cell in an animal.

Thus, the present invention further provides a vector comprising a nucleic acid of this invention. The vector can also include other amino acid-encoding nucleotide sequences. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols. The expression vector can comprise viral nucleic acid including, but not limited to, adenovirus, retrovirus and or adeno-associated virus nucleic acid. The nucleic acid or vector of this invention can also be in a liposome or a delivery vehicle which can be taken up by a cell via receptor-mediated or other type of endocytosis. The nucleic acid or vector of this invention can also be in a pharmaceutically acceptable carrier, as described below.

The caging group of the present invention can be any caging group which is photolabile, i.e., which undergoes a chemical reaction with a target molecule whereby the caging group covalently attaches to the target molecule (Walker et al, 1988), thereby inhibiting the biological activity of the target molecule, and which upon subsequent exposure to a radiation source (e.g., UV wavelength), undergoes a conformational change that breaks the covalent bond to the target molecule and restores the biological activity of the target molecule (e.g., nucleic acid, amino acid sequence).

The caging group of the present invention can be but is not limited to, DMNPE 1-(4,5-dimethyoxy-2-nitrophenyl) ethyl, (2-nitrophenyl) ethyl, 5-carboxymethoxy-2-nitrobenzyl, ((5-carboxymethoxy-2-nitrobenzyl)oxy) carbonyl, 4,5-dimethyoxy-2-nitrobenzyl, ((4,5-dimethoxy-2-nitrobenzyl)oxy) carbonyl, alpha-carboxy-2-nitrobenzyl, 1-(2-nitropheny) ethyl, 2-nitrobenzyl and Desoxybenzoinyl, as well as any other photolabile caging group now known or later developed which can covalently attach to a sequence of two or more nucleotides or to an amino acid sequence and reversibly inhibit the biological activity of the molecule or substance to which the caging group is attached. By "reversibly" is meant that the inhibitory effect of the caging group can be initiated by binding the caging group to a target molecule or substance and removed by exposing the caged molecule or substance to light, thereby altering the conformation of the caging group and restoring biological activity to the target molecule or substance. The caging groups listed herein are known in the art and can be routinely synthesized or purchased. Additional caging groups having the properties of the caging groups of this invention can be identified according to the protocols described herein and as described in the literature.

The caging group can be covalently bound to a target molecule by combining the caging group with a target molecule after activation of the caging group with an oxidant such as manganese oxide. As a result of the covalent bonding to a caging group, the physical structure of the target molecule is reversibly modified (e.g., the tertiary structure is altered in various ways, which can include coiling, looping and twisting), the bioactivity of the target molecule is reversibly inhibited (e.g., the stability of the target molecule in vivo is increased due to protection against nonspecific DNase or RNase enzymatic cleavage as well as protection against site-specific enzymes; and other biological processing molecules which act via recognition of DNA or RNA are blocked) and delivery of the caged molecule to cells is enhanced by greater affinity of binding with cell membranes or by enhanced binding to a delivery vehicle (e.g., liposome).

The type of irradiation for altering the conformation of the caging group on the target molecule and restoring biological activity to the target molecule can be, but is not limited to, light at a wavelength in a range from 300 to 700 nm and more preferably at a wavelength in a range from 300 to 400 nm and most preferably at a wavelength of 365 nm, as well as irradiation at other wavelengths, such as X-rays, magnetic resonance and thermal energy. The source of the irradiation can be any source by which a substance can be exposed to the radiation, including but not limited to, a lamp, a fiber optic device, a laser, an X-ray machine, a light emitting compound which can be ingested and a lithotripsy device which produces light by bubble collapse.

The caged nucleic acid of this invention can be used to target localized gene expression to a specific cell population after non-localized gene delivery to cells as well as to target localized blockade of normal expression pathways by caged anti-sense nucleic acids. In addition, the caged nucleic acid can be used in vitro as a light sensitive trigger for activation of the polymerase chain reaction (PCR) as an alternative to "hot start" PCR, for control of primer concentrations in PCR (e.g., light-activated nested PCR), for sequencing of DNA or RNA by differential bio-activation of 5' or 3' ends to allow selective cleavage of end nucleotides and for sequential activation using two or more different caging groups which are triggered to "uncage" sequentially or separately by different radiation stimuli. The caged nucleic acid of this invention can also be used either in vivo or in vitro for tracing post-transcriptional and/or post-translational events as well as for blockade of insertion of DNA or RNA intercalating dyes (e.g., pico green; ethidium bromide).

Because expression of the nucleic acid of this invention can be reversibly inhibited, the caged nucleic acid of this invention can be used to regulate expression of an exogenous nucleic acid within a cell. Thus, the present invention further provides a method of selectively expressing a nucleic acid in a cell, comprising: a) covalently linking the nucleic acid to a photolabile caging group which reversibly prevents expression of the nucleic acid; b) introducing the nucleic acid of step (a) into the cell; and c) exposing the cell of step (b) to light, whereby exposure to the light unlinks the nucleic acid and the caging group and the nucleic acid is selectively expressed in the cell. As used herein, "covalently linking or linked" means forming a covalent bond between the caging group and the target molecule.

The present invention also provides a method of selectively regulating the expression of an endogenous nucleic acid comprising: a) covalently linking an antisense nucleic acid or a nucleic acid encoding an antisense nucleic acid to a photolabile caging group which reversibly prevents expression of the nucleic acid; b) introducing the nucleic acid of step (a) into the cell; and c) exposing the cell of step (b) to light, whereby exposure to the light unlinks the nucleic acid and the caging group and the nucleic acid is present in the cell as an antisense nucleic acid or is expressed in the cell as an antisense nucleic acid which can bind to and inactivate a complementary endogenous nucleic acid within the cell.

Antisense technology is well known in the art and describes a mechanism whereby a nucleic acid comprising a nucleotide sequence which is in an a complementary, "antisense" orientation with respect to a coding or "sense" sequence of an endogenous gene is introduced into a cell, whereby a duplex forms between the antisense sequence and its complementary sense sequence. The formation of this duplex results in inactivation of the endogenous gene. Antisense nucleic acid can be produced for any endogenous gene for which the coding sequence has been or can be determined according to well known methods.

Antisense nucleic acid can inhibit gene expression by forming an RNA/RNA duplex between the antisense RNA and the RNA transcribed from a target gene. The precise mechanism by which this duplex formation decreases the production of the protein encoded by the endogenous gene most likely involves binding of complementary regions of the normal sense niRNA and the antisense RNA strand with duplex formation in a manner that blocks RNA processing and translation. Alternative mechanisms include the formation of a triplex between the antisense RNA and duplex DNA or the formation of a DNA-RNA duplex with subsequent degradation of DNA-RNA hybrids by RNAse H. Furthermnore, an antisense effect can result from certain DNA-based oligonucleotides via triple-helix formation between the oligomer and double-stranded DNA which results in the repression of gene transcription.

The antisense nucleic acid may be obtained by any number of techniques known to one skilled in the art. One method of constructing an antisense nucleic acid is to synthesize a recombinant antisense DNA molecule. For example, oligonucleotide synthesis procedures are routine in the art and oligonucleotides coding for a particular protein or regulatory region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins or regulatory regions can be synthesized by first constructing several different double-stranded molecules that code for particular regions of the protein or regulatory region, followed by ligating these DNA molecules together. Once the appropriate DNA molecule is synthesized, this DNA can be cloned downstream of a promoter in an antisense orientation. Techniques such as this are routine in the art and are well documented.

An example of another method of obtaining an antisense nucleic acid is to isolate that nucleic acid from the organism in which it is found and clone it in an antisense orientation. For example, a DNA or cDNA library can be constructed and screened for the presence of the nucleic acid of interest. Methods of constructing and screening such libraries are well known in the art and kits for performing the construction and screening steps are commercially available (for example, Stratagene Cloning Systems, La Jolla, Calif.). Once isolated, the nucleic acid can be directly cloned into an appropriate vector in an antisense orientation, or if necessary, be modified to facilitate the subsequent cloning steps. Such modification steps are routine, an example of which is the addition of oligonucleotide linkers which contain restriction sites to the termini of the nucleic acid. General methods are set forth in Sambrook et al. (1989).

The cell of this invention can be any cell which can incorporate and/or express exogenous nucleic acid and can be exposed to a form of radiation which allows for uncaging of the caging group. For example, the cell of this invention can be, but is not limited to, endothelial cells, epithelial cells and blood cells, as well as any other cell or population of cells (e.g., in an organ or tissue) in which nucleic acid could be selectively expressed according to the methods provided herein. lIn particular, the method of this invention can be used to selectively express nucleic acid in cells which are easily accessible such as lymphocytes, skiin cells and eye cells as well as cells which are internally located (e.g., lung cells accessible by fiber optics) to treat specific disorders associated with these cell types.

In the method of this invention, the nucleic acid can be delivered to the cells in vivo and/or ex vivo by a variety of mechanisms well known in the art (e.g., uptake of naked DNA, viral infection, liposome fusion, intramuscular injection of DNA via a gene gun, endocytosis and the like).

If ex vivo methods are employed, cells or tissues can be removed and maintained outside the body according to standard protocols well known in the art. The caged nucleic acid of this invention can be introduced into the cells via any gene transfer mechanism, such as, for example, virus-mediated gene delivery, calcium phosphate mediated gene delivery, electroporation, microinjection or proteoliposomes. The transduced cells can then be infused (e.g., in a pharmaceutically acceptable carrier) or homotopic ally transplanted back into a subject per standard methods for the cell or tissue type. Standard methods are known for transplantation or infuision of various cells into a subject.

For in vivo administration, the cells can be in a subject and the nucleic acid can be administered in a pharmaceutically acceptable carrier. The subject can be any animal in which it is desirable to selectively express a nucleic acid in a cell. In a preferred embodiment, the animal of the present invention is a human. In addition, non-human animals which can be treated by the method of this invention can include, but are not limited to, cats, dogs, birds, horses, cows, goats, sheep, guinea pigs, hamsters, gerbils and rabbits, as well as any other animal in which selective expression of a nucleic acid in a cell can be carried out according to the methods described herein.

In the method described above which includes the introduction of exogenous DNA into the cells of a subject (i.e., gene transduction or transfection), the nucleic acids of the present invention can be in the form of naked DNA or the nucleic acids can be in a vector for delivering the nucleic acids to the cells for expression of the nucleic acid inside the cell. The vehicle can be a commercially available preparation, such as an adenovirus vector (Quantum Biotechnologies, Inc. (Laval, Quebec, Canada). Delivery of the nucleic acid or vehicle to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vehicle of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (Pastan et al., 1988; Miller et al., 1986). The recombinant retrovirus can then be used to infect and thereby deliver nucleic acid to the infected cells. The exact method of introducing the nucleic acid into mammalian cells is, of course, not limited to the use of retroviral vectors. Other techniques are widely available for this procedure including the use of adenoviral vectors (Mitani et al., 1994), adeno-associated viral (AAV) vectors (Goodman et al., 1994), lentiviral vectors (Naidini et al., 1996) and pseudotyped retroviral vectors (Agrawal et al., 1996). Physical transduction techniques can also be used, such as liposome delivery and receptor-mediated and other endocytosis mechanisms (see, for example, Schwarzenberger et al., 1996). This invention can be used in conjunction with any of these or other commonly used gene transfer methods.

The nucleic acid and the nucleic acid delivery vehicles of this invention, (e.g., viruses; liposomes, plasmids, vectors) can be in a pharmaceutically acceptable carrier for in vivo administration to a subject. By "pharmaceutically acceptable" is meant a material that is not biologically or otherwise undesirable, i.e., the material may be administered to a subject, along with the nucleic acid or vehicle, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The nucleic acid or vehicle may be administered orally, parenterally (e.g., intravenously), by intramuscular injection, by intraperitoneal injection, transdermally, extracorporeally, topically or the like. The exact amount of the nucleic acid or vehicle required will vary from subject to subject, depending on the species, age, weight and general condition of the subject, the severity or mechanism of any disorder being treated, the particular nucleic acid or vehicle used, its mode of administration and the like. Thus, it is not possible to specify an exact amount for every nucleic acid or vehicle. However, an appropriate amount can be determined by one of ordinary skill in the art using only routine experimentation given the teachings herein (see, e.g., Martin, Remington's Pharmaceutical Sciences).

As one example, if the nucleic acid of this invention is delivered to the cells of a subject in an adenovirus vector, the dosage for administration of adenovirus to humans can range from about $10^7$ to $10^9$ plaque forming units (pfu) per injection, but can be as high as $10^{12}$ pfu per injection (Crystal, 1997; Alvarez, 1997).

Parenteral administration of the nucleic acid or vehicle of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The present invention additionally provides a polypeptide covalently linked to a photolabile caging group which prevents biological activity of the polypeptide. The polypeptide of this invention can be, but is not limited to, a phosphoprotein which regulates specified patterns of cell division and protein expression, a member of the AP-1 transcription family, a target protein within the MAP kinase cascade and a cyclin, which regulates cell cycle progression. Any protein involved in the cell's genetic process can be purified can be caged and photoactivated within a cell according to the present invention to regulate cell function in a temporally and spatially dependent manner.

For example, phosphorytated proteins can be photocaged, introduced into cells and targeted to exert an effect in a particular sub-population of cells in a temporally and spatially dependent manner by photolytic uncaging of the caged proteins. One particularly useful phosphoprotein which has been shown to be important in regulating protein expression in endothelial cells is the endogenous inhibitor of the NfkB system called IkB, or the inhibitor of the kB system. This protein normally binds to the NFkB heterodimer (p50, p65) or homodimer (p50,p50) and prevents the nuclear translocation of this transcription factor. The activation of IkB is mediated by its phosphorylation, which causes it to be released from IkB and allows the activation of the complex. Therefore, introduction of a photoactivatable form could be used to regulate this expression.

The caged protein of this invention can be produced according to the protocols described herein. The caged protein can be introduced into cells via a variety of mechanisms well known in the art for delivering proteins to the cytoplasm of a cell. For example, the cage protein can be introduced into the cell via liposome delivery, gene gun delivery, direct injection, endocytosis of a protein which binds the cell surface and the like.

As one example, the caged protein of this invention can be a fusion protein which comprises a caged polypeptide and a ligand which binds to and is internalized by cells which express a receptor for the ligand on the surface.

The ligand of the fusion protein can be any ligand which has the capability of binding to and becoming internalized by cells which express a receptor for the ligand, as determined by methods well known in the art. In this manner, the fusion protein of this invention can be targeted for internalization by specific cell populations which express the receptor which binds the ligand of the fusion protein.

The present invention further provides a nucleic acid encoding the fusion protein of this invention, a vector comprising the nucleic acid and a cell comprising the vector. The present invention also provides nucleic acids complementary to, or capable of, hybridizing with the nucleic acids encoding the fusion proteins of this invention.

Protocols for construction of a vector containing a nucleic acid encoding the fusion protein of this invention are well known in the art (see, e.g., Sambrook et al., 1989). The nucleic acids can be obtained from naturally occurring sources or the nucleic acids can be synthesized. The nucleic acid encoding the fusion protein can be placed into an expression vector, which can be obtained commercially or produced in the laboratory.

A variety of vectors and prokaryotic and eukaryotic expression systems such as bacteria, yeast, filamentous fungi, insect cell lines, bird, fish, transgenic plant and mammalian cells, among others, are known to those of ordinary skill in the art and can be used in the present invention.

Thus, the present invention further contemplates a method of producing the fusion protein of the present invention, comprising introducing a vector encoding the fusion protein into a cell under conditions whereby the nucleic acid encoding the fusion protein is expressed and the fusion protein is produced; and isolating and purifying the fusion protein. Isolation and purification of the fusion protein can be carried out by protocols well known to those of skill in the art.

The nucleic acid sequences can be expressed in cells after the sequences have been operably linked to, i.e., positioned, to ensure the functioning of an expression control sequence. These expression vectors are typically replicable in the cells either as episomes or as an integral part of the cell's chromosomal DNA. Commonly, expression vectors can contain selection markers, e.g., tetracycline resistance, hygromycin resistance, gentarnicin resistance or methotrexate resistance, to permit detection and/or selection of those cells transformed with the desired nucleic acid sequences (see, e.g., U.S. Pat. No. 4,704,362).

The caged protein or fusion protein of the present invention can be administered to cells either ex vivo or in vivo in the same manner as described herein for the caged nucleic acids of this invention. Thus, the caged polypeptide or fusion protein of this invention can be in a pharmaceutically acceptable carrier, as defined herein and can be administered to a subject, which is preferably a human, in accordance with the methods described herein.

Thus, the present invention further provides a method of selectively activating a polypeptide in a cell, comprising: a) covalently linking the polypeptide to a photolabile caging group which reversibly prevents biological activity of the polypeptide; b) introducing the polypeptide of step (a) into the cell; and c) exposing the cell of step (b) to light, whereby exposure to the light unlinks the polypeptide and the caging group and the polypeptide is selectively activated in the cell.

The present invention is more particularly described in the following examples which are intended as illustrative only since numerous modifications and variations therein will be apparent to those skilled in the art.

EXAMPLES

Example I.

Caged DNA has the same light absorbance characteristics as commercially available caged ATP. Spectral scans of DMNEcaged ATP and DMNPE caged GFP plasmid show the same absorbance shifts at 390 and 260 nm, consistent with the release of caged material.

Caged ATP: DMNE (1-(4,5-dimethyoxy-2-nitrophenyl) ethyl estercaged ATP (Molecular Probes, Eugene, Oregon) was dissolved in water at a concentration of 2 mg/ml and scanned for absorbance from 190 mnm to 1100 nm on a Beckmran DU640 scanning spectrophotometer. The cuvette contents were then exposed to light on an Ultra Lum light box with a surface irradiance of 9,000 $\mu W/cm^2$ for 10 minutes and the material was re-scanned. The two absorbance peaks were shifted to the right with the absorbance spectrum showing an increase in absorbance at 390 nm and at 260 nm.

Caged plasmid expressing gene for green fluorescent protein (GFP). The caged plasmid encoding GFP (pGreen Lantern, Life Technologies) was prepared by reaction with (4,5-dimnethoxy-2-nitroacetophenone hydrazone) activated by manganese (IV) oxide as follows below.

Caged oligonucleotide (15 mer). The caged oligonucleotide was prepared by reaction with (4,5-dimethoxy-2-nitroacetophenone hydrazone) activated by manganese (IV) oxide as follows:

Caging procedure: Caging is achieved with three reagents: A (4,5-dimethoxy-2-nitroacetophenone hydrazone), B (Manganese (IV) oxide), and C (Celit™ (diatomaceous earth)). The caging solution is prepared as follows: 25 mg of (A) is dissolved in 1 ml of DMSO. To this, 100 mg of manganese oxide (oxidant) is added and the mixture is stirred at room temperature for 30 minutes. The final solution is pressure filtered through 100 mg of Celitem to remove the oxidant. The filter is rinsed with 250 ml increments of DMSO until the wash is colorless. The caging solution is wrapped in foil to limit exposure to light.

The activated caging solution in 150 $\mu l$ DMSO is combined with the nucleic acid (100–150 $\mu g$) in 300 $\mu l$ water or TE buffer and held at room temperature for 20 minutes or at 4° C. for 24 hours. The same procedures can be applied for producing caged polypeptides.

Separation procedures. Caged materials (nucleic acids or proteins) are separated from unreacted caging groups by two phase extraction using an equal volume of chloroform with the reaction mixture. The extracted material is lyophilized and re-suspended in TE buffer. Caged materials can also be separated from unreacted caging groups by electrophoretic separation on a gel (either agarose or polyacrylamide), as well as by chromatography, TLC with silica gel and/or HPLC according to protocols well known in the art.

Photo-activation (photolysis). UV light sources (e.g., hand-held long UV light source; UV gel box light source) can be utilized to achieve uncaging. A laser source can also be used to minimize exposure of cells and tissues to non-activating wavelengths.

Caged samples were exposed to UV light from a hand held long wavelength UV lamp with a peak output of 365 nm and an irradiance of 8900 $\mu$W/cm$^2$ at 10 inches. Exposure was at six inches for 20 minutes.

The same results as described above for caged ATP were observed with DMNPE caged plasmid encoding GFP (0.02 $\mu$g/ml) and caged oligonucleotide. Identical shifts in the spectrum were observed with an increase in absorbance at 390 and 260 nm. These biochemical data demonstrate that the caging of GFP plasmid DNA and single-stranded oligonucleotide DNA produces a light reactive caged compound with the same light absorbing characteristics as demonstrated for commercially prepared caged ATP.

Example 2

DNase I is reversibly blocked by DMNPE caging of calf thymus DNA. DNase I (Sigma), an enzyme which randomly cleaves DNA, was reconstituted to 80 Kunitz of DNase I per 1 ml of cold 0. 15M NaCl. Calf thymus DNA (Sigma) was prepared in water. Just prior to use, 25 ml of sodium acetate (pH 5) and 12.5 ml of Mg(SO$_4$) were added to the DNA solution. Ultra-pure H$_2$O was added to make the final diluted volume of DNA solution 250 ml. Preparation of caging solution was carried out as described above and 1.5 ml was added to 20 ml of the DNA solution. The DNA and caging solution mixture was allowed to combine for 30 minutes. Some of the mixture containing the caged DNA was placed in a cuvette for exposure to UV light. A UV lamp (Cole Parmer B-100A with a peak output of 365 nm and an irradiance of 8900 $\mu$W/cm$^2$ at 10 inches was placed six inches directly above the cuvettes containing the caged DNA for 10 minutes. Pico Green® (ex 480 nm, em 520 nm, Molecular Probes, Eugene, OR), which is an interchelating dye which only fluoresces in a chain of nucleotides, was used to follow the progressive cleavage of the DNA by DNase I by fluorescence spectroscopy (Perkin Elmer, LS50B). The changes in fluorescence of three samples were measured simultaneously in a rotating cuvette adapter for 10 minutes. Fluorescence decreased over time as the enzyme cleaved the DNA strands in the cuvette containing uncaged DNA as a control. The rate at which DNase I digested uncaged DNA was compared with the rate at which the enzyme digested DNA which had been caged and with caged DNA which had been exposed to 5 minutes of UV light.

DNase I was observed to normally degrade uncaged DNA but was unable to digest caged DNA which had no UV exposure. However, digestion activity was restored after the caged DNA was exposed to UV light, which removed the caging compound from the DNA, allowing digestion by DNase I to proceed. These data demonstrate that DMNPE caging of DNA reversibly alters DNA structure to prevent digestion by DNase I.

Example. 2.5

Caging of plasmid nucleic acid alters its electrophoretic mobility. Caged plasmid encoding GFP was prepared as described herein. The caged plasmid was divided into two samples. One sample was irradiated as described herein and the other caged sample was not irradiated. The samples were run on a 1% agarose gel. The caged samples which were not irradiated were altered in their electrophoretic mobility in comparison with the caged plasmids which were irradiated. These data indicate that caging of the plasmid alters the electrophoretic mobility of the nucleic acid either by altering the charge characteristics of the nucleic acid or by altering the tertiary structure of the nucleic acid.

Example 3

Caging of plasmid DNA blocks cutting of DNA by the restriction enzyme BamH I. The restriction endonuclease BamH I cleaves at a single site of the 5.0 kb plasmid pGreen Lantern (PGFP; Life Technologies). The effectiveness of cleavage by this enzyme was compared with caged pGFP plasmid and caged pGFP plasmid that was subsequently exposed to 20 minutes of 365 mn light. Restriction enzyme cleavage was carried out for 16 hours at 37° C. and the DNA was visualized on a 1% agarose gel.

In the resulting gel, the lane containing caged plasmid which was exposed to light showed a greatly enhanced band corresponding in molecular weight to the cleavage product, as compared to the lane containing caged plasmid which was not exposed to light. These data demonstrate that the restriction site on the caged plasmid was protected from cleavage by Bam HI and that the restriction site became accessible to the enzyme upon photoactivation of the caging group by exposure to light.

The conditions under which the nucleic acid is bound to the caging group can be optimized in order to maximize the number of nucleic acid molecules which become caged. For example, this can be done by optimizing the molar ratio of caging group to nucleic reactive sites. A series of molar ratios can be tested for optimizing the amount of caging. In particular, to optimize caging to a plasmid containing a restriction site which is to be protected from a restriction endonuclease by caging the plasmid, caged plasmid can be produced in a series of reactions in which molar ratios of caging group to nucleic acid base pairs from 8:1 to 100:1 are employed. The resulting caged plasmids can be exposed to enzyme before and after exposure to light to quantitatively determine the degree of plasmid caging and thus identify the optimal molar ratio of caging group to plasmid.

Furthermore, the optimal wavelength for activating the caging groups of this invention can be determined according to methods well known in the art as well as according to the methods described herein.

To quantitate the sensitivity limits of measuring low levels of caging, a series of caging reactions can be carried out with varying ratios of reactive caging group to plasmid. Each caged sample can be scanned with a spectrophotometer and then rescanned after uncaging by exposure to 10 minutes of UV light. These results can be compared to absorbance spectrum changes observed with decreasing amounts of commercially obtained caged ATP (Molecular Probes). From these data, the number of released caging groups can be determined based on the manufacturer's estimate that 89% of the commercially prepared caged ATP product is caged, with one caging group per ATP.

A more sensitive measure of caging is to use different radioactive labels on the caging group (e.g., $^{14}$C) and on the plasmid (e.g., $^{3}$H). The ratio of the different radioisotopes can be measured in the caged sample.

Example 3.5

Synthesis of mRNA from caged plasmid can be activated by light in vitro. Caged pTRI-xef can reversibly block synthesis of mRNA in an in vitro assay of transcription. A linearized TRIPLEscript plasmid containing the 1.85 kb Xenopus elongation factor gene (pTRI-xef; supplied with the MEGAscript In Vitro Transcription Kit, Ambion Inc., Austin, Tex., cat#1330) can serve as the control template for transcription. DMNPE-caged and "never caged" pTRI-xef templates can be incubated for 2 hours at 37° C. in the enzyme cocktail supplied with the kit. Immediately prior to incubation, one of the caged samples can be exposed to 20 minutes of UV light as described herein. Production of transcribed message can be assayed by denaturing agarose gel electrophoresis.

Example 4

Plasmid expression is induced by light activation after delivery to cultured cells or tissue. Caged pSV β-galactosidase (Promega) reversibly blocks protein production in HeLa cells. Two duplicate 6 well plates of HeLa cells were liposome-transfected with either pSV β-galactosidase plasmid or DMNPE caged pSV β-galactosidase plasmid. After transfection, cells were incubated for 24 hours and then one six well plate of HeLa cells was exposed to 10 minutes of UV light as described herein. At 24 hours following UV exposure, all cultures were fixed and stained to visualize expression of the β-galactosidase protein.

Never caged plasmid and light exposed caged plasmid produced similar staining patterns while the caged plasmid showed reduced staining. These data demonstrate that caging noticeably reduces the number of cells producing a dark blue stain which is characteristic of the production of the intracellular protein β-galactosidase. Expression is increased by exposure to 365 nm light, due to re-activation of caged plasmid.

Example 5

Expression of cagedplasmid can be activated by light following gene gun delivery to the corneal epithelial layer. Caging of pSV β-galactosidase plasmid reversibly blocks the production of the protein β-galactosidase in corneal epithelial cells. Corneas from New Zealand white albino rabbits were placed in an organ culture medium for 5 days prior to gene transfer. LacZ with SV40 promoter (Promega) was used as a reporter gene. The Accell Pulse Gun (gene gun; Auragen Inc., Middleton, Wis.) delivered gold particles with either DMNPE caged or "never" caged plasmids to the cultured corneas with blasts of helium at 250 psi. The caging compound was removed from the plasmids of the transfected corneas by exposure to UV light for 15 min as described herein. At 24 hrs after transfection, the corneas were stained for LacZ expression.

A low level of expression of β-galactosidase was detected in corneas transfected with caged pSV β-galactosidase plasmid. Tissue containing caged pSV β-galactosidase plasmid which was exposed to UV light showed a dramatic increase in the expression of β-galactosidase. The highest level of LacZ expression was seen in the corneas transfected with control plasmids and the lowest expression was seen in corneas with caged plasmid without UV light exposure. Corneas transfected with either control or caged plasmids and exposed to UV exhibited similar intermediate expression levels. These data demonstrate that expression of caged plasmid can be activated by light following gene gun delivery to the corneal epithelial layer. These data also demonstrate that it is possible to control the expression of DNA after delivery to a tissue.

Example 6

Expression of caged GFP in HeLa cells is increased by exposure to light. HeLa cells were transfected in 35 mm wells in Optimem 16–18 h after seeding into 35 mm petri dishes at 20,000 cells/cm². Cells were washed with serum-free DMEM medium before transfection. Each well was transfected with 2 μg of pGreen Lantern plasmid which was caged as described herein and complexed with 12 μg of liposomes (0.1 μm dia, DOTAP:DOPE, 1:1) for 15 min. before transfection. The cationic liposomes containing DOTAP and DOPE were prepared by vacuum evaporation followed by extrusion to yield unilamellar liposomes of 0.1 mm as previously described (Tseng et al., 1996). Six hours after transfection, the DNA-liposome transfection solution was replaced with medium containing 10% calf serum. At that time, selected wells were exposed to 365 nin light for 20 min. 48 hours post-transfection, cells were washed with cold CMF-PBS, trypsinized (0.25%) and fixed in paraformaldehyde (1%) for 10 min at room temperature. The fixed cells were washed with CMF-PBS containing 1% formaldehyde three times, resuspended in CMF-PBS containing 1% formaldehyde and stored at 4° C. for flow cytometric analysis. Transfection samples were analyzed by a FACSCalibur (Becton-Dickinson) flow cytometer equipped with an argon laser argon exciting at a wavelength of 488 nm. For each sample, 20,000 events were collected in list-mode.

Analysis of the results of these experiments showed that a large number of HeLa cells produced green fluorescent protein (GFP) when the plasmid was not caged and that caging reduced this expression significantly. After light exposure, the expression of GFP was increased. These data demonstrate that caging reduced expression of the plasmid and subsequent exposure to light increased expression of the plasmid in comparison to caged plasmids which were not exposed to light.

Example 7

Activation of caged marker protein expression in rats by light. Caged plasmid pCEP 4 coding for luciferase and containing the SV40 Poly A signal (100 μg; prepared as described herein) can be dried onto 1 nm gold beads and delivered intradermally to shaved rat skin with a 400 psi helium pulse from an Accell pulse gun. After delivery the area can be allowed to heal for 24 hours. At the end of this period, some areas can be exposed to 365 nm light from a hand held UV-A lamp (Cole-Parmer) for 20 min or to a laser beam at 355 nm for a very brief period (e.g., less than one second). At 24 after light treatment, skin plugs can be removed and assayed for luciferase activity in a scintillation counter.

Example 8

Activation of marker protein in rabbit retinal endothelium. Caged green fluorescent protein plasmid can be prepared as described herein. The plasmid can be complexed with DOTAP:DOPE 0.1 μm liposome in a 6:1 ratio. Delivery to rabbit retinal endothelium can be achieved with intravascular administration of the liposome complex into the ophthahnic artery. One rabbit eye can be exposed to 365 nm light and the other can be shielded. Fluorescence angiographic examination can be carried out 24 hours later. Expression can be targeted within the retina of a single eye by directing laser light to specific regions in a manner similar to that used currently to ablate specific vessels.

Example 9

Treatment of psoriasis by targeted expression of junction proteins in psoriatic lesions. Caged plasmid coding for the junction protein cadherin-5 can be combined with DOTAP- :DOPE liposome in a ratio of 6:1 and applied to regions of psoriatic tissue or injected subdermally into surrounding regions of a psoriatic lesion. After transfection, the non-psoriatic region around the psoriatic lesion can be shielded and the area irradiated with 365 nm light (8900 $\mu$W/cm$^2$ at 10 inches) for 20 min or with a laser beam as described herein. By this approach, selected endothelial cells (e.g., those within vessels of the psoriatic lesions) can be transfected with cadherin-5 plasmid and exposed to light, resulting in the production of additional cadherin-5 protein which can disrupt the efflux of lymphocytes by restricting their transvascular passage out of the vessels in the psoriatic region. Once the efflux of lymphocytes has been disrupted, the psoriatic lesions will revert to normal morphology.

Example 10

In vivo treatment of diabetic retinopathy with caged junction protein cadherin-5. Caged plasmid coding for the junction protein cadherin-5 can be combined with DOTAP:DOPE liposome in a ratio of 6:1. Delivery to human retinal endothelium can be achieved with intravascular administration of the liposome complex into the ophthalmic artery. After transfection, the regions of the retinal microvascular which are observed to leak sodium fluorescein under fluorescent angiography can be targeted with 355 nm laser light. In retinal endothelial cells transfected with cadherin-5 plasmid and exposed to light, additional cadherin-5 protein can be produced which can repair the local leak by providing additional cell-cell regions of interaction and disrupt the efflux of proteins and solutes, thereby stabilizing and/or reversing diabetic breakdown of retinal blood vessels.

Example 11

Stabilization of anti-sense oligonucleotides. Plasmid coding for green fluorescent protein (GFP) can be transfected into HeLa cells along with caged anti-sense nucleotide (prepared as described herein) which is antisense to a region of the coding green fluorescent coding plasmid. After 24, 48 and 72 hours, one culture of cells can be exposed to 355 nm light for 20 minutes. Cells containing caged anti-sense and plasmid for GFP will express GFP. Cells containing caged anti-sense GFP, plasmid GFP and exposed to light will not express GFP due to the hybridization of the plasmid with anti-sense oligonucleotide. Preservation of the anti-sense nucleic acid from endonuclease as described herein is demonstrated by comparing expression of GFP encoding nucleic acid delivered in combination with nucleic acid which is anti-sense to GFP. Without caging protection of the anti-sense nucleic acid, GFP expression in the cell will increase over time as the unprotected anti-sense nucleic acid is degraded by endonucleases.

Example 12

Biological effects of light or the released cage compound on transfected cells. The effects of various forms and intensities of irradiation on humans is well documented in the literature. Some biological effects due to released cage material have been reported (Kaplan et al., 1978). In the present invention, the effects of exposure to light in the wavelength required to uncage the molecules of this invention as well as the effects of released caging groups within a cell can be determined according to methods well known in the art for determining the effects of radiation on cells and tissues as well as the effects of foreign materials within cells with regard to toxicity and pathological effects.

Initial experiments to determine these effects on cells can be dye exclusion protocols wherein the amount of cell lysis as well as effects on cell growth can be measured by automated cell counting (e.g., Coulter™ counting) of treated cells. Additional experiments can include re-infasion of cells transfected with caged nucleic acid or protein into an experimental animal model and uncaging of the nucleic acid or protein by exposure to light as described herein.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

REFERENCES

Agrawal et al. "Cell-cycle kinetics and VSV-G pseudotyped retrovirus mediated gene transfer in blood-derived CD34$^+$ cells." *Exp. Hematol.* 24:738–747 (1996).

Alvarez, R. D. and D. T. Curiel. 1997. A phase I study of recombinant adenovirus vector-mediated delivery of an anti-erbB-2 single chain (sFv) antibody gene from previously treated ovarian and extraovarian cancer patients. *Hum. Gene Ther.* 8:229–242.

Andres A-C et al. Ha-ras oncogene expression directed by a milk protein gene promoter: tissue specificity, hormonal regulation, and tumor induction in transgenic mice. Proc. Nat. Acad. Sci. 84:1299–1303, 1987.

Brown R H and Miller J B. Progress, problems and prospects for gene therapy in muscle. Curr. Op. Rheumatology 8(6):539–543, 1996.

Crystal, R. G. 1997. Phase I study of direct administration of a replication deficient adenovirus vector containing *E. coli* cytosine deaminase gene to metastatic colon carcinoma of the liver in association with the oral administration of the pro-drug 5-fluorocytosine. *Human Gene Therapy* 8:985–1001.

Eden S and Cedar H. Role of DNA methylation in the regulation of transcription. Curr. Opin. Gen. Dev. 4:255–259, 1994.

Eden S and Cedar H. Role of DNA methylation in the regulation of transcription. Curr. Opin. Gen. Dev. 4:255–259, 1994.

Furth PA et al., Temporal control of gene expression in transgenic mice by a tetracycline-responsive promoter. Proc. Nat. Acad. Sci. 91:9302–9306, 1994.

Goodman et al. "Recombinant adeno-associated virus-mediated gene transfer into hematopoietic progenitor cells." Blood 84:1492–1500 (1994)

Gossen M et al., Transcriptional activation by tetracyclines in mammalian cells. Science 268:1766–1769, 1995.

Hart IR. Tissue specific promoters in targeting systemically delivered gene therapy. Seminars in Oncology. 23(1):154–8, 1996.

Hynes N E, Kennedy N, Rahmsdorf U and Groner B. Hormone-responsive expression of an endogenous proviral gene of mouse mammary tumor virus after molecular cloning and gene transfer into cultured cells. Proc. Nat. Acad. Sci. 78(4):2038–2042, 1981.

Ishihara A, Gee K, et al. Photoactivation of caged compounds in single living cells: an application to the study of cell locomotion. Biotechniques 23:268–274, 1997.

Kaplan, J. H. Forbush, B. and Hoffman, J. F., Rapid photolytic release of ATP protected analogue: utilization by the Na:K pump of human red blood cell ghosts. *Biochemistry* 17:1929–1935, 1978.

Lee H C, Aarhus R, Gee K R and Kestner T. Caged nicotinic acid adenine dinucleotide phosphate. J. Biol. Che. 272(7): 4172–4178, 1997.

Lewin, "Genes V" Oxford University Press Chapter 7, pp. 171–174 (1994).

Manthrope, M, et al. Gene therapy by intramuscular injection of plasmid DNA: studies on firefly luciferase gene expression in mice. Human Gene Therapy 4(4): 419–431, 1993.

Martin, E. W. (ed.) Remington 's Pharmaceutical Sciences, latest edition. Mack Publishing Co., Easton, Pa.

Mayo, K E, WanTen, R and Palmiter R D. The mouse metallothionine-I gene is transcriptionally regulated by cadmium following transfection into human or mouse cells. Cell 29:99–108, 1982.

McCray, James A., et.al. "Properties and Uses of Photoreactive Caged Compounds." *Annual Review of Biophysics & Biophysical Clhemistry* 18: 239–270, 1989.

McGall, G, Labadie J et al., Light-directed synthesis of high-density oligonucleotide arrays using semiconductor photoresistors. Proc. Nat. Acad. Sci. 93:13555–13560, 1996.

Michieli, P., Li, W., Lorenzi, M. V., Miki, T., Zakut, R., Givol, D., and Pierce, J. H. *Oncogene* 12, 775–784, 1996.

Miller et al. Redesign of retrovirus packaging cell lines to avoid recombination leading to helper virus production. *Mol. Cell Biol.* 6:2895, 1986.

Mitani et al. Transduction of human bone marrow by adenoviral vector. *Human Gene Therapy* 5:941–948 (1994).

Naidini et al. "In vivo gene delivery and stable transduction of nondividing cells by a lentiviral vector." *Science* 272:263–267 (1996)

No, D, Yao, T-P and Evans, RM. Ecdysone-inducible gene expression in mammalian cells and transgenic mice. Proc. Nat. Acad. Sci. 93:3346–3351, 1996.

Pastan et al. A retrovirus carrying an MDR1 cDNA confers multidrug resistance and polarized expression of P-glycoprotein in MDCK cells. *Proc. Nat. Acad. Sci.* 85:4486, 1988.

Patton W F, Alexander J S et al. Mercury-arc photolysis : a method for examining second messenger regulation of endothelial cell monolayer integrity. Anal. Biochem. 196:31–38, 1991.

Ramsahoye B H, Davies, C S and Mills, K I. DNA methylation: biology and significance. Bolld Rev. 10:249–261, 1996.

Rosenfeld M A, Ronald G, Crystal R G. Gene therapy for pulmonary diseases. Pathologie Biol. 41(8):677–680, 1993.

Sambrook et al., *Molecular Cloning: A Laboratory Manual*. 2nd Ed., Cold Spring Harbor Laboratory, Cold Spring Harbor, N.Y. (1989)

Schwarzenberger et al. "Targeted gene transfer to human hematopoietic progenitor cell lines through the c-kit receptor." *Blood* 87:472–478 (1996).

Searle P F, Stuart, G W and Palmiter R D. Building a metal-responsive promoter with synthetic regulatory elements. Molecul. Cell. Biol. 5(6):1480–1489, 1985.

Stein G S, Stein J L, Lian J B, van Wijnen A J. Montecino M. Functional interrelationships between nuclear structure and transcriptional control:

contributions to regulation of cell cycle- and tissue-specific gene expression. J. of Cell. Biochem. 62(2): 198–209, 1996.

Torchilin VP. Affinity liposomes in vivo: factors influencing target accumulation. J. Molecular Recog. 9:335–346, 1996.

Tseng, W., N. B., Haselton, F. R., Giorgio, T. D. Transfection by cationic liposomes using simultaneous measurements of plasmid delivery and gene expression, J. Biol. Chem. (in press, 1997).

Tseng, W., Purvis, N. B., Haselton, F. R., Giorgio, T. D. Cationic liposomal delivery of plasmid to endothelial cells measured by quantitative flow cytometry. *Biotechnology and Bioengineering* 50:548–554, 1996.

Walker J W, Reid G P, McCray J A and Trentham D R. Photolabile 1-(2-Nitrophenyl)ethyl phosphate esters of adenine nucleotide analogues. Synthesis and mechanism of photolysis. J. Am. Che. Soc. 110:7170–7177, 1988.

Wootton J F and Trentham D R. Caged compounds to probe the dynamics of cellular processes: Synthesis and properties of some novel photosensitive P-2-nitrobenzyl esters of nucleotides. In *Photochemnical Probes in Biochemistry*, PE Nielson (ed), Kluwer Acad. Pub., Norwell, Mass., pp 277–296, 1988.

Yarranton, GT. Inducible vectors for expression in mammalian cells. Curr. Op. Biotech. 3:506–511, 1992.

What is claimed is:

1. An isolated nucleic acid covalently linked to a photolabile caging group which reversibly prevents expression of the nucleic acid, wherein the caging group is 1-(4,5-dimethyoxy-2-nitrophenyl) ethyl.

2. A vector comprising the nucleic acid of claim 1.

3. A cell comprising the vector of claim 2.

4. The nucleic acid of claim 1 in a pharmaceutically acceptable carrier.

5. The vector of claim 2 in a pharmaceutically acceptable carrier.

* * * * *